United States Patent
Sweeney et al.

(10) Patent No.: US 10,098,584 B2
(45) Date of Patent: Oct. 16, 2018

(54) PATIENT HEALTH IMPROVEMENT MONITOR

(75) Inventors: Robert J. Sweeney, Woodbury, MN (US); Ramesh Wariar, Blaine, MN (US); Julie A. Thompson, Circle Pines, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 950 days.

(21) Appl. No.: 13/366,473

(22) Filed: Feb. 6, 2012

(65) Prior Publication Data

US 2012/0203092 A1    Aug. 9, 2012

Related U.S. Application Data

(60) Provisional application No. 61/440,583, filed on Feb. 8, 2011.

(51) Int. Cl.
| | |
|---|---|
| *A61B 5/053* | (2006.01) |
| *A61B 5/00* | (2006.01) |
| *A61B 5/11* | (2006.01) |
| *A61B 5/024* | (2006.01) |
| *A61B 5/08* | (2006.01) |

(Continued)

(52) U.S. Cl.
CPC ............ *A61B 5/4833* (2013.01); *A61B 5/053* (2013.01); *A61B 5/1118* (2013.01); *A61B 5/6831* (2013.01); *A61B 5/0002* (2013.01); *A61B 5/0031* (2013.01); *A61B 5/024* (2013.01); *A61B 5/08* (2013.01); *A61B 2560/0431* (2013.01);

(Continued)

(58) Field of Classification Search
CPC ... A61B 5/0002; A61B 5/6801; A61B 5/6831; A61B 5/6832–5/6833; A61B 5/74; A61B 5/4833; A61B 5/1118
USPC ....... 600/390, 382, 373, 372, 391–392, 301, 600/547; 128/898
See application file for complete search history.

(56) References Cited

U.S. PATENT DOCUMENTS

4,842,266 A * 6/1989 Sweeney, Sr. ......... A63B 22/02
  482/54
6,161,095 A * 12/2000 Brown ................ G06F 19/3418
  705/2

(Continued)

FOREIGN PATENT DOCUMENTS

| EP | 1079733 B1 | 9/2009 |
|---|---|---|
| WO | WO-2007050435 A2 | 5/2007 |
| WO | WO-2010104978 A2 | 9/2010 |

OTHER PUBLICATIONS

Clark, "The Couch-to-5k Running Plan" in ActiiveNetwork (www.coolrunning.com), Oct. 25, 2006.*

*Primary Examiner* — Lee S Cohen
*Assistant Examiner* — Erin M Cardinal
(74) *Attorney, Agent, or Firm* — Schwegman Lundberg & Woessner, P.A.

(57) ABSTRACT

Systems and methods to monitor an improvement of a subject's physiological condition using a goal improvement profile are described. In an example, a physiological condition of a subject can be compared to a goal improvement profile, where the profile includes at least one target condition indicative of an improved physiological condition detectable using a physiological sensor signal, and a target time when the subject is expected to reach the target (Continued)

condition, where the comparison can be used to indicate whether the subject has met the target condition by the target time.

22 Claims, 6 Drawing Sheets

(51) Int. Cl.
  *A61N 1/362* (2006.01)
  *A61N 1/365* (2006.01)
  *A61N 1/37* (2006.01)

(52) U.S. Cl.
  CPC ........ *A61N 1/3627* (2013.01); *A61N 1/36521* (2013.01); *A61N 1/3702* (2013.01)

(56) References Cited

U.S. PATENT DOCUMENTS

| | | | |
|---|---|---|---|
| 6,290,646 B1 | 9/2001 | Cosentino et al. | |
| 6,478,736 B1* | 11/2002 | Mault | A61B 5/044 128/921 |
| 6,852,080 B2 | 2/2005 | Bardy | |
| 6,904,312 B2 | 6/2005 | Bardy | |
| 6,908,437 B2 | 6/2005 | Bardy | |
| 7,188,151 B2 | 3/2007 | Kumar et al. | |
| 7,258,670 B2 | 8/2007 | Bardy | |
| 7,273,454 B2 | 9/2007 | Raymond et al. | |
| 7,297,108 B2 | 11/2007 | Iliff | |
| 7,299,087 B2 | 11/2007 | Bardy | |
| 7,308,309 B1 | 12/2007 | Koh | |
| 7,310,551 B1 | 12/2007 | Koh et al. | |
| 7,314,451 B2 | 1/2008 | Halperin et al. | |
| 7,433,853 B2 | 10/2008 | Brockway et al. | |
| 7,468,032 B2 | 12/2008 | Stahmann et al. | |
| 7,577,475 B2 | 8/2009 | Cosentino et al. | |
| 7,598,878 B2 | 10/2009 | Goldreich | |
| 2003/0176808 A1* | 9/2003 | Masuo | 600/547 |
| 2004/0077934 A1* | 4/2004 | Massad | A61B 5/1135 600/300 |
| 2006/0064030 A1* | 3/2006 | Cosentino et al. | 600/547 |
| 2007/0015974 A1* | 1/2007 | Higgins et al. | 600/300 |
| 2007/0055169 A1* | 3/2007 | Lee | A61B 5/0006 600/544 |
| 2008/0086318 A1* | 4/2008 | Gilley | G06Q 10/06 705/319 |
| 2008/0161651 A1 | 7/2008 | Peterson et al. | |
| 2008/0200774 A1 | 8/2008 | Luo | |
| 2008/0208015 A1 | 8/2008 | Morris et al. | |
| 2008/0221928 A1 | 9/2008 | Garcia et al. | |
| 2008/0228090 A1 | 9/2008 | Wariar et al. | |
| 2008/0319282 A1 | 12/2008 | Tran | |
| 2009/0036828 A1 | 2/2009 | Hansen et al. | |
| 2009/0069720 A1* | 3/2009 | Beck | A61B 5/4866 600/587 |
| 2009/0076343 A1 | 3/2009 | James et al. | |
| 2009/0076344 A1 | 3/2009 | Libbus et al. | |
| 2009/0076405 A1* | 3/2009 | Amurthur et al. | 600/529 |
| 2009/0088606 A1 | 4/2009 | Cuddihy et al. | |
| 2009/0124917 A1 | 5/2009 | Hatlestad et al. | |
| 2009/0163774 A1 | 6/2009 | Thatha et al. | |
| 2009/0233770 A1* | 9/2009 | Vincent | A63B 24/0021 482/8 |
| 2009/0234410 A1 | 9/2009 | Libbus et al. | |
| 2009/0247836 A1* | 10/2009 | Cole et al. | 600/301 |
| 2010/0052892 A1 | 3/2010 | Allen et al. | |
| 2010/0099954 A1* | 4/2010 | Dickinson | A61B 5/0006 600/300 |
| 2010/0205008 A1 | 8/2010 | Hua et al. | |
| 2010/0261987 A1* | 10/2010 | Kamath | A61B 5/14532 600/365 |
| 2011/0040572 A1* | 2/2011 | Chmiel | A61B 5/0002 705/2 |
| 2011/0145747 A1* | 6/2011 | Wong et al. | 715/771 |
| 2011/0301916 A1* | 12/2011 | Oshima et al. | 702/173 |
| 2012/0277763 A1* | 11/2012 | Greenblatt | A61B 18/12 606/130 |

\* cited by examiner

PATIENT HEALTH IMPROVEMENT MONITOR

CLAIM OF PRIORITY

This application claims the benefit of priority under 35 U.S.C. § 119(e) of Sweeney et al., U.S. Provisional Patent Application Ser. No. 61/440,583, entitled "PATIENT HEALTH IMPROVEMENT MONITOR", filed on Feb. 8, 2011, which is herein incorporated by reference in its entirety.

BACKGROUND

Patient monitoring systems can be used to automate the monitoring of a patient's physiological condition. In clinical settings, such as hospitals, such monitoring systems can allow a treating clinician to more efficiently manage the care of one or more patients, such as by providing centralized access to the physician information about the physiological condition of one or more patients. A remote monitoring system can allow a patient to live at home or in an extended-care facility while still allowing close supervision of the patient's physiological condition by the treating clinician. Such remote monitoring systems can communicate to a centralized system through a communications link, such as using a communication or computer network.

Systems and methods to measure patient compliance by receiving or detecting one or more indications of a patient action in response to an instruction, and analyzing the indications to calculate a measurement representative of the patient's ability to follow the instruction are described in commonly assigned U.S. Patent Application 2008/0161651 entitled "Surrogate Measure of Patient Compliance."

A hospitalization management system that includes a heart failure analyzer to receive diagnostic data representative of one or more physiological signals sensed from a patient and assesses the risk of rehospitalization for the patient is described in commonly assigned U.S. Patent Application 2008/0228090 entitled "Method and Apparatus for Management of Heart Failure Hospitalization."

OVERVIEW

While under a clinician's care, a patient can receive a treatment, such as a therapy in response to a clinical event, or a modification of a drag regimen, such as to manage a chronic health condition. The patient can also receive advice or instructions intended to improve the patient's overall health or prevent a re-occurrence of a health condition. For example, the patient can be advised to begin an exercise program or modify a diet plan. In such cases, the clinician may rely on the patient to follow medical instructions and to report the results of the treatment. However, the patient can fail to comply with the treatment plan or can fail to report whether the treatment worked as expected. Thus, a patient being readmitted to receive care in a hospital or other urgent setting can be the clinician's first indication that the patient did not progress as expected.

The present inventors have recognized, among other things, a need for systems and methods to monitor an improvement of a subject's physiological condition, such as using a goal improvement profile. In an example, a physiological condition of a subject can be compared to a goal improvement profile. The profile can include at least one target condition indicative of an improved physiological condition detectable using a physiological sensor signal, and a target time when the subject is expected to reach the target condition. The comparison can be used to indicate whether the subject has met the target condition by the target time.

Example 1 can include subject matter (such as a system, a method, a means for performing acts, or a machine-readable medium including instructions that, when performed by the machine, cause the machine to perform acts, etc.) that can include a comparison circuit and an indication generator circuit. The comparison circuit can be configured to compare a physiological condition of a subject to a goal improvement profile. The goal improvement profile can include: (1) at least one target condition indicative of an improved physiological condition detectable using a physiological sensor signal; and (2) a target time when the subject is expected to reach the at least one target condition. The indication generator circuit can be configured to generate an improvement indication indicating whether the subject will meet the target condition by the target time.

In Example 2, the subject matter of Example 1 can optionally include a goal improvement profile generator that can be configured to create the goal improvement profile for the subject using at least one of physiological data history of the subject, physiological data of a population that is comparable to the subject, or clinician input.

In Example 3, the subject matter of one or any combination of Examples 1-2 can optionally be configured such that the target condition includes an expected improvement to the physiological condition of the subject in response to a therapy provided by a caregiver.

In Example 4, the subject matter of one or any combination of Examples 1-3 can optionally be configured such that the expected improvement to the physiological condition of the subject includes an improvement in response to a treatment for a heart failure event.

In Example 5, the subject matter of one or any combination of Examples 1-4 can optionally be configured such that the goal improvement profile includes a goal improvement path over time between a start time and the target time, wherein the goal improvement path includes the at least one target condition.

In Example 6, the subject matter of one or any combination of Examples 1-5 can optionally be configured such that the comparison circuit can compare the physiological condition of the subject to the goal improvement path at one or more times between the start time and the target time to determine a progress parameter. The progress parameter can be indicative of whether the physiological condition of the subject is progressing towards reaching the target condition by the target date.

In Example 7, the subject matter of one or any combination of Examples 1-6 can optionally be configured such that the indication generator circuit can generate an indication using the progress parameter. The indication can indicate whether the physiological condition of the subject is progressing towards reaching the at least one target condition by the target time.

In Example 8, the subject matter of Examples 1-7 can optionally include an ambulatory physiological sensor, a communication circuit, and a memory circuit. The ambulatory physiological sensor can be configured to determine a physiological condition of the subject using an excitation signal, the excitation signal capable of being received at one or more locations. The communication circuit can be configured to receive one or more physiological sensor signals, wherein the physiological sensor signals are representative of a determined physiological condition of the subject. The memory circuit can be configured to store the goal improvement profile.

In Example 9, the subject matter of one or any combination of Examples 1-8 can optionally be configured such that the physiological sensor can communicate a physiological sensor signal representative of the physiological condition of the subject determined from the excitation signal, wherein the physiological sensor signal can be communicated using the excitation signal as a carrier.

Example 10 can include subject matter (such as a system, a method, a means for performing acts, or a machine-readable medium including instructions that, when performed by the machine, cause the machine to perform acts, etc.) that can include a comparison circuit, an indication generator circuit, at least two electrodes, and an adhesive band. The comparison circuit can be configured to compare a physiological condition of a subject to a goal improvement profile. The goal improvement profile can include: (1) at least one target condition indicative of an improved physiological condition detectable using one or more physiological sensor signals; and (2) a target time when the subject is expected to reach the at least one target condition. The indication generator circuit can be configured to generate an improvement indication, wherein the improvement indication indicates whether the subject will meet the target condition by the target time. The at least two electrodes can be configured to sense an impedance-indicating signal at the skin of the subject to provide the physiological sensor signal. The adhesive band can be configured to secure the comparison circuit, the indication generator circuit, and the electrodes to the subject, such that the apparatus can be configured to be capable of providing the improvement indication from an ambulatory subject and without requiring a tether to the subject.

In Example 11, the subject matter of Example 10 can optionally be configured to include a communication circuit that can be configured to communicate the improvement indication using at least one of an audible or a visual indicator.

In Example 12, the subject matter of one or any combination of Examples 10-11 can optionally be configured such that the communication circuit can be remotely communicatively coupled, via a computer or communications network, to communicate the improvement indication.

Example 13 can include, or can be combined with the subject matter of one or any combination of Examples 1-12 to optionally include, subject matter (such as an apparatus, a method, a means for performing acts, or a machine-readable medium including instructions that, when performed by the machine, cause the machine to perform acts) that can comprise: automatically comparing a determined physiological condition to a goal improvement profile that includes: (1) at least one target condition indicative of an improved physiological condition detectable using a physiological sensor signal, and (2) a target time when the subject is expected to reach the at least one target condition; and automatically generating an improvement indication indicating whether the subject has met the target condition by the target time.

In Example 14, the subject matter of one or any combination of Examples 1-13 can optionally include creating the goal improvement profile for the subject using at least one of a physiological data history of the subject, physiological data of a population that is comparable to the subject, or clinician input.

In Example 15, the subject matter of one or any combination of Examples 1-14 can optionally include creating a goal improvement path over time between a start time and the target time, wherein the goal improvement path includes the at least one target condition.

In Example 16, the subject matter of one or any combination of Examples 1-15 can optionally include comparing the physiological condition of the subject to the goal improvement path at one or more times between the start time and the target time to determine a progress parameter, wherein the progress parameter is indicative of whether the physiological condition of the subject is progressing towards reaching the target condition by the target date.

In Example 17, the subject matter of one or any combination of Examples 1-16 can optionally include generating an indication using the progress parameter, the indication indicating whether the physiological condition of the subject is progressing towards reaching the at least one target condition by the target time.

In Example 18, the subject matter of one or any combination of Examples 1-17 can optionally include determining a post-decompensation heart failure decompensation status of a subject using a physiological sensor signal.

In Example 19, the subject matter of one or any combination of Examples 1-18 can optionally include receiving the physiological sensor signal from a sensor configured to be associated with the subject.

In Example 20, the subject matter of one or any combination of Examples 1-19 can optionally include extracting the physiological sensor signal from an excitation signal, the excitation signal configured to determine a characteristic associated with the physiological condition of the subject.

These examples can be combined in any permutation or combination. This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
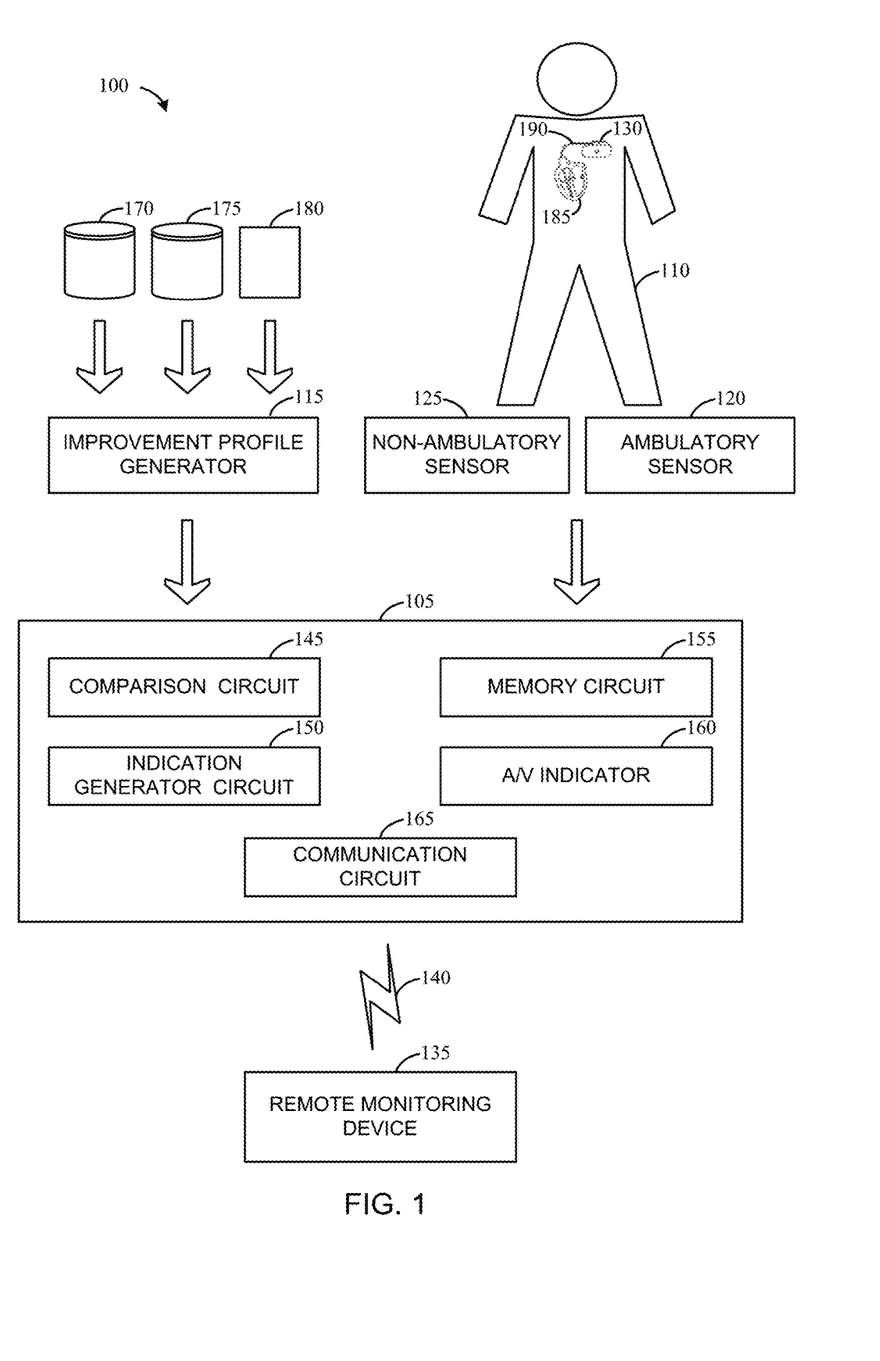
FIG. 1 shows an example of a block diagram of portions of an example of a system to monitor an improvement to a subject's physiological condition.

FIG. 1 shows an example of a block diagram of portions of an example of a system 100 that can be configured to monitor an improvement to a subject's physiological condition. In an example, the system 100 can include an ambulatory or non-ambulatory medical device, such as can include a goal improvement monitor 105, an improvement profile generator 115, and at least one of an external ambulatory sensor 120, a non-ambulatory sensor 125, or an implantable ambulatory sensor, such as an implantable medical device (IMD) 130 configured to sense at least one physiological signal indicative of a physiological condition of the subject 110. The system 100 can optionally include a remote monitoring device 135 that can be configured to communicate to the goal improvement monitor 105 using a communication link 140, such as a communication network or a computer network. In an example, the goal improvement monitor 105 can include a comparison circuit 145, an indication generator circuit 150, a memory circuit 155, an audio/visual indicator 160, and a communication circuit 165. In an example, the goal improvement monitor 105 can be configured to predict whether a treatment goal, such as a goal improvement profile, can be met, or detect whether the treatment goal has been met.

In an example, the subject 110 can visit a clinician to receive treatment or a therapy, such as a therapy designed to improve a physiological condition (e.g., a treatment in response to a clinical event or illness), to manage or control an ongoing health condition (e.g., a drug therapy to manage a chronic medical condition or genetic condition), to maintain the subject's overall health (e.g., a recommendation, such as resulting from an appointment for routine preventative care, a physical exam, etc.), or to seek advice to improve a physiological condition (e.g., an exercise program, a diet plan, etc.). As a result of the treatment or therapy, the clinician may expect the subject's physiological condition to meet a target condition by a target time, such as to improve the subject's physiological condition, (e.g., a reduction in fever, a weight loss, a reduction in side effects, etc.) or to maintain the current physiological condition (e.g., a stable physiological condition following a reduction in dosage or other change to a drug therapy). A target condition and corresponding target time can be specified as part of a goal improvement profile, such as can be generated by the improvement profile generator 115. In an example, a goal improvement profile can be a single specified target condition to be reached within a specified target time, a specified group of target conditions to all be reached by a specified target time, or a specified group of target conditions associated with respective (optionally different) target times. Some examples of goal improvement profiles are discussed in greater detail below, such as in conjunction with FIGS. 2A-2B.

In an example, the improvement profile generator 115 can automatically generate a goal improvement profile for a subject, such as by using at least one of a physiological data history 170 of the subject 110, physiological data of a population 175 that is comparable to the subject 110, or clinician input 180. In an example, the goal improvement generator 115 can be communicatively coupled to the comparison circuit 145 of the goal improvement monitor 105, such as to provide a goal improvement profile to the comparison circuit 145. The improvement profile generator 115 can be located with the goal improvement monitor 105, remotely therefrom, or incorporated therein.

The comparison circuit 145 can be used to compare a goal improvement profile to a physiological condition of the subject 110. The physiological condition can be determined using one or more physiological sensor signals received from a physiological sensor associated with the subject 110, such as the ambulatory sensor 120, the non-ambulatory sensor 125, or a sensor associated with the IMD 130. Examples of the non-ambulatory sensor 125 can include a weight scale, a blood analyte (e.g., gas concentration) sensor, or a respiratory sensor device, such as can include an airflow sensor. Examples of the ambulatory sensor 120 can include a heart sounds sensor, an accelerometer, a cardiac impedance sensor, a posture sensor, an acoustic sensor (e.g., microphone), a respiration sensor, a transthoracic or intra-cardiac impedance sensor, a pressure sensor, an activity sensor, or an external respiratory band sensor such as having piezoelectric or other sensor elements. In an example, the physiological condition can be determined using one or more physiological characteristics of the subject, such as heart rate, heart rate variability, heart rate variability footprint, autonomic balance, or physiologic response to activity (e.g., respiration, heart-rate, heart sounds, transthoracic impedance, intra-cardiac impedance, etc.). In an example, the physiological condition can be determined using a combination of one or more physiological sensor signals and one or more physiological characteristics. In an example, an ambulatory sensor 120 can be included in or associated with an IMD, such as the IMD 130.

In an example, the comparison circuit 145 can be communicatively coupled to an indication generator circuit 150. The indication generator circuit 150 can be configured to generate an improvement indication that can indicate whether the physiological condition of the subject 110 has met or can meet the goal improvement profile. The indication generator circuit 150 can be communicatively coupled to an audio/video (A/V) indicator circuit, such as the A/V indicator 160. The A/V indicator 160 can be configured to provide a user with an audible or visual representation of the goal improvement indication. In an example, the A/V indicator 160 can be configured to provide an audible representation of the goal improvement indication (e.g., a buzzer, an audio message, etc.), or a visual representation of the goal improvement indication (e.g., a light, an email, a report, etc). In an example, the A/V indicator 160 can include a device for displaying information such as a graphical user interface (GUI) configured to display information.

In an example, the goal improvement monitor 105 can include a communication circuit 165, such as to permit wired or wireless communication with an external device, such as the remote monitoring device 135, improvement profile generator 115, ambulatory sensor 120, non-ambulatory sensor 125, or IMD 130, such as using a communications link 140. In an example, the communications link 140 can include a communications or computer network, a direct wired connection, an inductive communication link, a radio-frequency (RF) link, or any combination.

In an example, the remote monitoring device 135 can be located remotely, such as to provide an audible or visual indication of the goal improvement indication associated with the subject 110, such as using the A/V indicator 160 discussed above.

The system 100 can include processing capability, such as within the goal improvement monitor 105, improvement profile generator 115, ambulatory sensor 120, non-ambulatory sensor 125, IMD 130, or remote monitoring device 135, such that various functions or methods discussed in this document can be implemented at any of such locations, or tasks of such functions or methods can be distributed between two or more of such locations. In an example, portions of the goal improvement monitor 105, such as the comparison circuit 145, the indication generator circuit 150, the memory circuit 155, the A/V indicator 160, or the communication circuit 165 can be implemented in hardware, software, or firmware, such as using an application-specific integrated circuit (ASIC) constructed to perform one or more particular functions, or a general-purpose circuit programmed to perform such functions. Such a general-purpose circuit can include a microprocessor, a microcontroller, or a programmable logic circuit, or a portion of one or more of these.

Figure 2A:
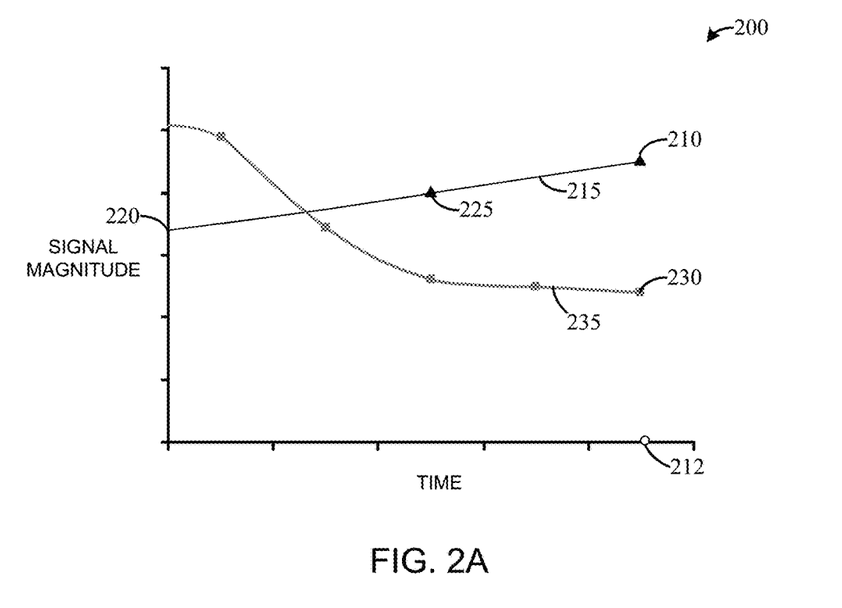
FIG. 2A shows a graph of an example of a goal improvement profile.
Figure 2B:
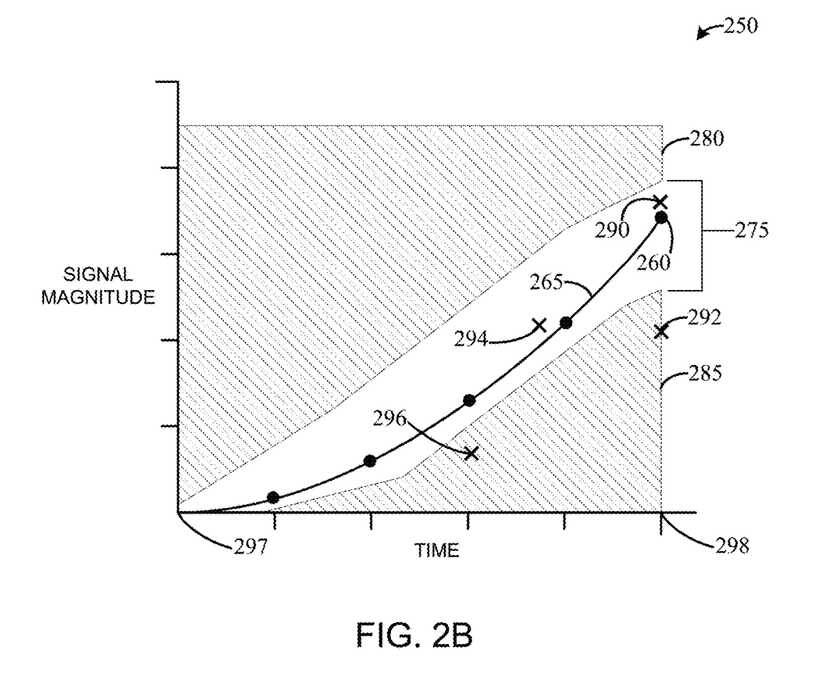
FIG. 2B shows a graph of an example of a goal improvement profile.

FIGS. 2A-2B show graphs of examples of a goal improvement profiles. In FIG. 2A-2B, the examples of goal improvement profiles 200, 250, are shown such that the x-axis represents time and the y-axis represents an indication of a measurable physiological condition of the subject 110. In an example, a goal improvement profile 200 can be represented as a point 210 specifying a target condition to be reached by a corresponding specified target time 212. In an example, the goal improvement profile 200 can be a goal improvement path, such as a linear path 215 or a curvilinear path 235. The discrete or continuous goal improvement paths 215 and 235 can be specified over time between a starting physiological condition 220 (e.g., the physiological condition of the subject 110 at the time of therapy, the physiological condition of the subject 110 at a specified time after receiving the therapy, or the physiological condition of the subject 110 at a specified time before receiving the therapy) and the target condition 210 to be reached by the corresponding specified target time 212. In an example, a comparison circuit, such as comparison circuit 145, can compare the physiological condition of the subject 110 to the goal improvement path 215 at an intermediate time such as to assess whether the physiological condition of the subject is progressing towards meeting the target condition 210, such as at the point 225. In an example, an improvement profile 200 can have two or more target conditions 210, 230, two or more target paths 215, 235, or a combination of target conditions and target paths. In an example, a goal improvement profile 200 can be specified to contain a single target condition for a physiological condition of the subject, such as a target weight loss to be met within a specified time duration. In an example, the goal improvement profile 200 can be specified to contain two or more target conditions, each target condition having an associated time duration to meet the associated target condition, such as a target weight loss and a target thoracic impedance.

In FIG. 2B, a goal improvement profile 250 can include a target condition or a goal improvement path, such as the target condition 260 or the goal improvement path 265, either or both of which can be specified using an improvement window 275. A detected indication representative of a physiological condition can be deemed to meet the target condition or goal improvement path if it falls within the improvement window 275. In an example, the improvement window 275 can be defined as the region (e.g., at a particular time) or area (e.g., over a period of time) between an upper threshold, such as the shaded area 280, and a lower threshold, such as the shaded area 285.

In an example, a subject can suffer from an acute heart failure event and can receive treatment from a caregiver, such as a diuretic regimen therapy, to relieve symptoms of heart failure and to control fluid retention. For example, a subject can receive a therapy (e.g., the diuretic regimen) that can be configured to alleviate a thoracic fluid overload condition. The target condition 260 can represent a targeted increase in thoracic impedance (representing a decrease in the thoracic fluid overload) to be reached by the target time elapsed after receiving therapy. In an example, if a measured indication of the thoracic fluid status physiological condition 290 falls within the improvement window 275, the goal improvement monitor 105 can indicate that the subject 110 did meet the target condition. However, if the measured physiological condition 292 falls outside the improvement window 275, the goal improvement monitor 105 can indicate that the subject 110 did not meet the target condition 260.

Similarly, the goal improvement monitor 105 can indicate that the subject 110 is progressing towards meeting the target condition, such as at 294, or is not progressing towards the target condition, such as at 296. In an example, the comparison circuit 145 can be configured to compare the physiological condition of the subject to the goal improvement profile 265 at one or more times between a start time 297 and the target time 298 to generate a progress parameter (e.g., a Boolean indication, a variable, etc.). For example, the subject can receive a diuretic therapy, where the goal improvement path corresponds to a continuous path representative of the targeted increase in thoracic impedance between the start time 297 (e.g., the beginning of the diuretic therapy) and the target time 298 (e.g., the time where the subject is expected to reach the target impedance goal). In an example, not pictured, the goal improvement profile can include two or more discrete points between or including the start time 297 and the target time 298. In an example, if a measured indication of the thoracic fluid status physiological condition 294 falls within the improvement window 275, the goal improvement monitor 105 can indicate that the subject 110 is progressing towards meeting the target condition. However, if the measured physiological condition 296 falls outside the improvement window 275, the goal improvement monitor 105 can indicate that the subject 110 is not progressing towards the target condition 260.

Figure 3:
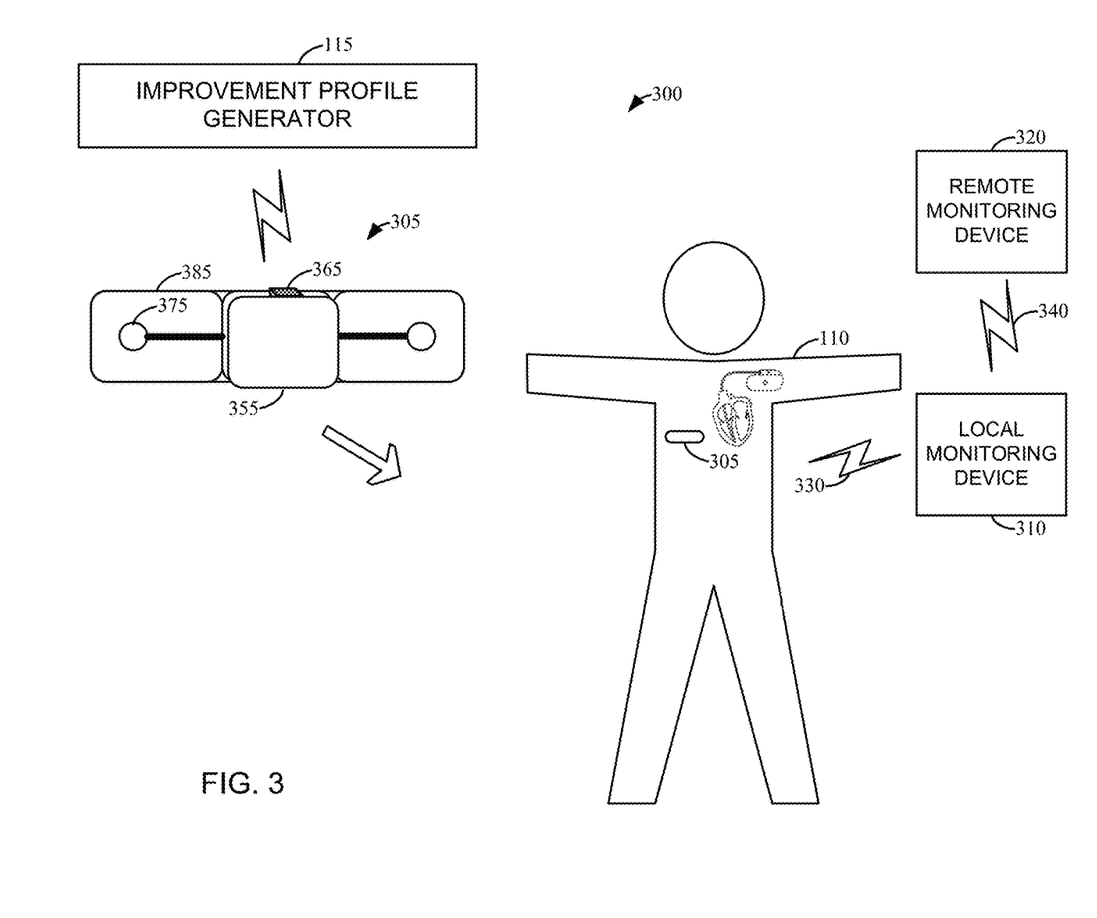
FIG. 3 shows an example of a block diagram of portions of an example of a system to monitor an improvement of a subject's physiological condition.

FIG. 3 shows an example of a block diagram of portions of an example of a system 300 that can be configured to monitor an improvement of a subject's physiological condition. In an example, the system 300 can include a goal improvement monitor 305. The goal improvement monitor 305 can be configured to communicate to a monitoring device (e.g., the local monitoring device 310 or the remote monitoring device 320), such as using one or more communication links, (e.g., the communication link 330-340). In an example, the goal improvement monitor 305 can include a processor circuit 355, an improvement indicator 365, two or more electrodes 375, and an attachment mechanism 385, such as an adhesive band. In an example, the processing module 355 can include or be coupled to any of the comparison circuit 145, the indication generator circuit 150, the memory circuit 155, the A/V indicator 160, or the communication circuit 165.

The attachment mechanism 385 (e.g., an adhesive band, an elastic band, a necklace, a tether, a bracelet, a watch band, etc.) can be used to physically associate the goal improvement monitor 305 to the ambulatory subject 110 such that the goal improvement monitor 305 can receive a physiological sensor signal representative of a physiological condition of the subject, such as from the ambulatory sensor 120, the non-ambulatory sensor 125, or the IMD 130. In an example, the attachment mechanism 385 can be configured to affix the goal improvement monitor to the subject 110 such that the electrodes 375 can be communicatively coupled to a sensing device through the skin of the subject using the body as a conductor. The electrodes 375 can be configured to receive an impedance indicating signal from an ambulatory or implanted sensor. Additionally or alternatively, the goal improvement monitor 305 can be configured to receive a physiological sensor signal from an ambulatory or non-ambulatory sensor using a communication link, such as using a communication circuit 165 to communicate through an RF link, a telemetry link, or a communication or computer network.

As discussed above, the goal improvement monitor 305 can be configured to receive a goal improvement profile from an improvement profile generator 115 and to generate a goal improvement indication. In an example, the goal improvement monitor 305 can be configured provide an improvement indication to the subject 110 such as by using the improvement indicator 365. In an example, an audible or visual indication provided by the improvement indicator 365 can be configured to prompt the subject 110 to contact a clinician, such as to schedule a follow-up appointment. In an example, the goal improvement monitor 305 can be configured to provide the audible or visual indication to a user such as to a clinician, such as by using the local monitoring device 310, the remote monitoring device 320, or in any combination of the improvement indicator 365, the local monitoring device 310, or the remote monitoring device 320.

The goal improvement monitor 305 can be configured to store information associated with the physiological condition of the subject 110 onto a memory, such as the memory circuit 155. The stored information can include one or more goal improvement profiles, data associated with the physiological condition of the subject (e.g., a physiological sensor signal and the time at which the signal was collected), or the improvement indication. In an example, the stored information can be communicated to a monitoring device (e.g., the local monitoring device 310 or remote monitoring device 320) such as for processing, storage, or display. For example, the goal improvement monitor can communicate the information to the local monitoring device 310 or the remote monitoring device 320 using one or more of the communication links 330-340. In an example, the goal improvement monitor 305 can be sent to a remote location, such as a clinician's office or a hospital, for analysis and providing the goal improvement indication to a clinician or other user.

Figure 4:
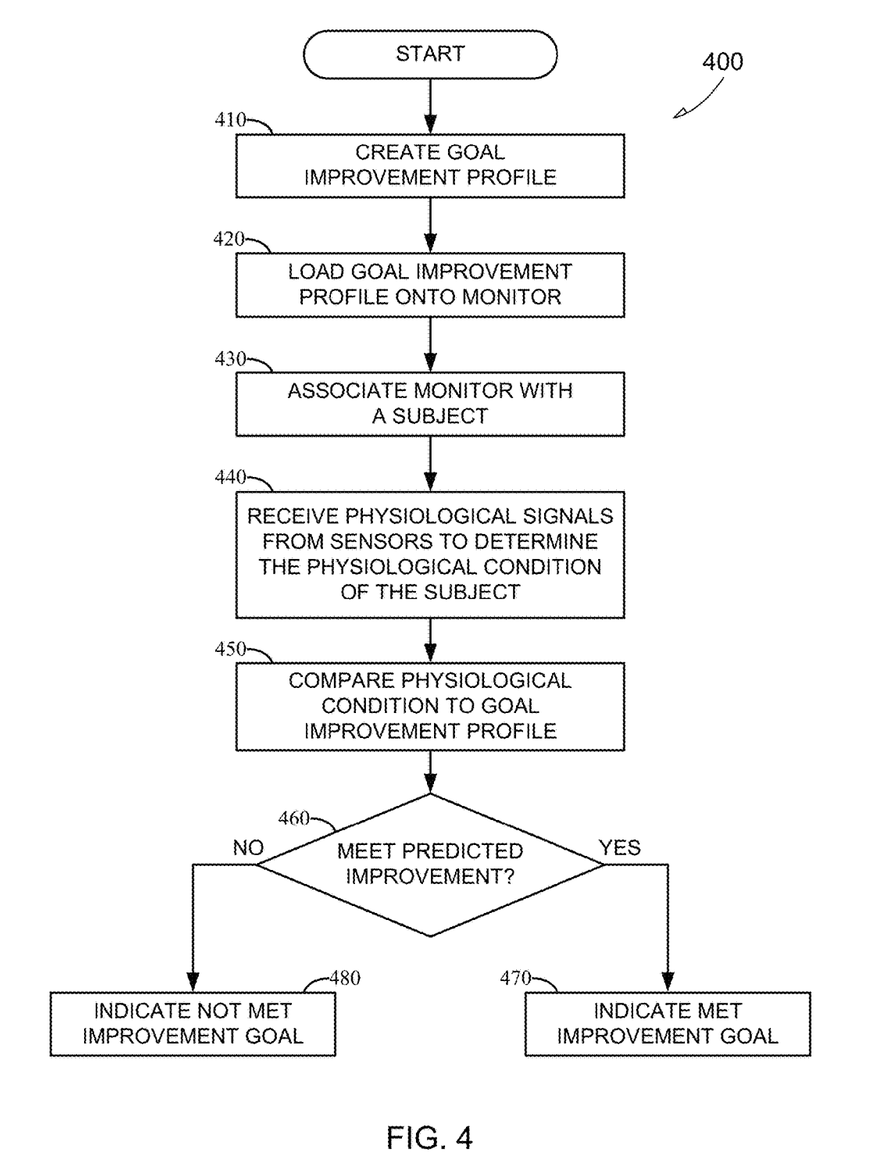
FIG. 4 shows an example of a method to predict or detect whether a subject will meet a goal improvement.

FIG. 4 shows an example of a method 400 to predict or detect whether a subject 110 will meet a target condition within the target time. At 410, a goal improvement profile can be created, such as by the improvement profile generator 115. The improvement profile generator 115 can generate the goal improvement profile using at least one of physiological data history 170 of a subject 110, a physiological data set of a population 175, or clinician input 180. At 420, the goal improvement profile generated by the goal improvement generator 115 can be provided to a goal improvement monitor 105, 305, such as to a memory circuit 155, for use by a comparison circuit 145. The goal improvement profile can be transferred to the goal improvement monitor 105, 305 through a communication link 140, 330-340, such as using a programmer.

At 430, the goal improvement monitor 105, 305 can be associated with the subject 110. In an example, the goal improvement monitor 105, 305 can include a non-ambulatory device, such as the local monitoring device 310 or the remote monitoring device 320, or can include an ambulatory device, such as the IMD 130 or the goal improvement monitor 305. In an example, a non-ambulatory goal improvement monitor 105 can be configured to receive a physiological sensor signal indicative of the physiological condition of the subject 110. In an example, an ambulatory goal improvement monitor 305 can be affixed to the subject 110, such as using the attachment mechanism 385, or can be included in an implantable device, such as the IMD 130. In an example, the goal improvement monitor 105, 305 can be configured as at least a portion of a remote monitoring device 320. The remote monitoring device 320 can be configured to receive a physiological sensor signal indicative of the condition of the subject 110 using the communication link 140, 330-340.

At 440, the goal improvement monitor 105, 305 can receive a physiological sensor signal to determine a physiological condition of the subject 110. In an example, the goal improvement monitor 105, 305 can receive a physiological sensor signal through electrodes, such as the electrodes 375 in contact with the skin of the subject 110. In an example, the goal improvement monitor 105, 305 can receive the physiological sensor signals through a communication link 140, 330-340. In an example, the goal improvement monitor 105, 305 can be configured to determine the physiological sensor signals directly, such as by using an integrated sensor. In an example, the goal improvement monitor 105, 305 can receive an indication of a physiological condition determined at another device. For example, a remote monitoring device 320 can be configured in part as the goal improvement monitor 105 and can be configured to receive the indication of the physiological condition of the subject 110 determined by the local monitoring device 310.

At 450, the goal improvement monitor 105, 305 can compare the determined indication of the physiological condition of the subject 110 to the goal improvement profile, such as using the comparison circuit 145. In an example, the comparison circuit 145 can compare the physiological condition of a subject to the target condition at a specified target time as specified in the goal improvement profile. In an example, the comparison circuit 145 can compare a physiological condition of the subject to the goal physiological condition, such as a goal improvement path, at one or more times, up to and including the target time. The comparison circuit 145 can compare the progress of the subject's indicated physiological condition to the goal improvement profile to assess the progress made towards reaching the target condition.

At 460, the goal improvement monitor 105, 305 can indicate whether the physiological condition of the subject 110 has met the target condition set in the goal improvement profile by the target time. In an example, indication circuit 150 can analyze the comparison from the comparison circuit 145 to determine whether the physiological condition of the subject 110 has met the target condition by the target time. The indication circuit 150 can be configured to indicate whether the subject's indicated physiological condition meets the target condition (e.g., directly meeting or exceeding the target condition, meeting a specified condition within a specified window around the target condition), or whether the subject's indicated physiological condition indicates progress towards meeting the target condition. If the subject's indicated physiological condition meets the target condition, then at 470 the goal improvement monitor 105, 305 can indicate to a user that the target condition has been met, such as using the A/V indicator circuit 160. In an example, the A/V indicator circuit 160 can indicate to a user (e.g., the subject 110, a clinician, etc.) that the target condition has been met through an audible or visual indication, such as a buzzer, a light, or a message.

Otherwise, at 480, the goal improvement monitor 105, 305 can indicate to the user that the physiological condition of the subject has not reached the target condition within the target time or is not expected to meet the target condition within the target time. For example, the A/V indicator circuit 160 can indicate to a user (e.g., the subject 110, a clinician, etc.) that the target condition has not been met using an audible or visual indication different than the audible or visual indication from step 470.

Figure 5:
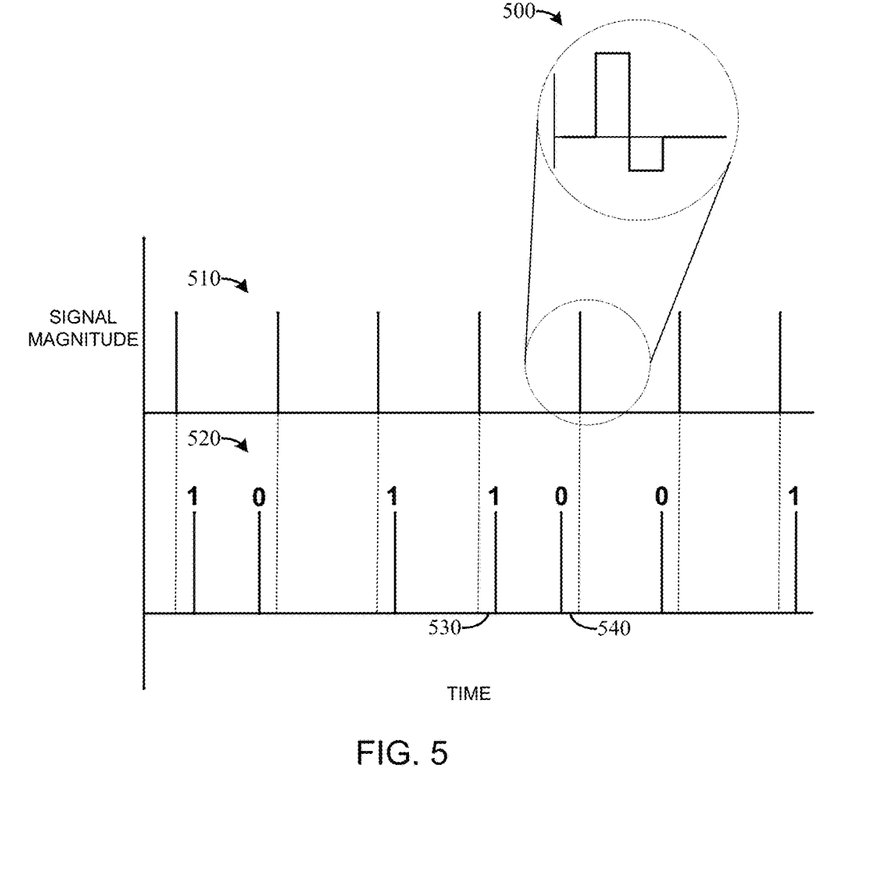
FIG. 5 illustrates an example of encoding information within an impedance indicating signal.

FIG. 5 illustrates an example of including information using an impedance indicating signal as a carrier signal and is shown such that the x-axis represents time and the y-axis represents a magnitude of the signal. In an example, an IMD 130 can be configured to sense a physiological characteristic of a subject 110, such as using a sensor integrated into the IMD 130, using the lead 190 such as positioned within or on heart 185, or communicating to one or more external sensors (e.g., the external ambulatory sensor 120, the non-ambulatory sensor 125, an implantable sensor, etc.). For example, IMD 130 can be configured to sense an electrical impedance value within the thoracic cavity, such as to measure minute ventilation, cardiac stroke volume, heart rate, respiration rate, thoracic fluid status, or one or more other impedance-derived characteristics of the subject 110. Systems and methods to measure transthoracic impedance are described in the commonly assigned U.S. Pat. No. 7,092,757 entitled "Minute Ventilation Sensor with Dynamically Adjusted Excitation Current," which is incorporated herein by reference in its entirety, including its description of using an excitation current to measure the impedance between two sense electrodes.

In an example, the IMD 130 can be configured to sense transthoracic impedance between an electrode on the can of the IMD 130 and an electrode on the lead 190 using a series of excitation pulses (e.g., two to four 50 microsecond pulses, two to four pulses at 20 Hz), such as the example of the excitation pulses 500. In an example, the excitation pulses 500 used to determine the transthoracic impedance of the subject 110 can be sensed at another location (e.g., at the skin of the subject 110), such as by the electrodes 375. In an example, external sensing, such as sensing the excitation waveform at the skin of the subject 110, can be done alternatively or in addition to sensing the transthoracic impedance by the IMD 130. Because the signal can be sensed at the electrodes 375, the IMD 130 can be configured to transmit to the electrodes 375 a physiological sensor signal (or other information) encoded, embedded or otherwise included with the excitation current waveform.

In an example, a periodic excitation waveform generator can use a clock pulse to create a periodic frequency for sending the excitation pulses 500, such as illustrated in the periodic excitation signal 510. The periodic excitation signal 510 can be configured to be used as carrier signal for a data-carrying signal, such as the binary data signal 520. In an example, the binary data signal 520 can be configured to use the periodic excitation signal 510, such that a data bit sent a time difference 530 after to the periodic excitation signal 510 can be a logical '1', whereas a data bit sent a time difference 540 before the periodic excitation signal 510 can be a logical '0.' The magnitudes of the time differences 530-540 can be configured to the same or different values.

Figure 6A:
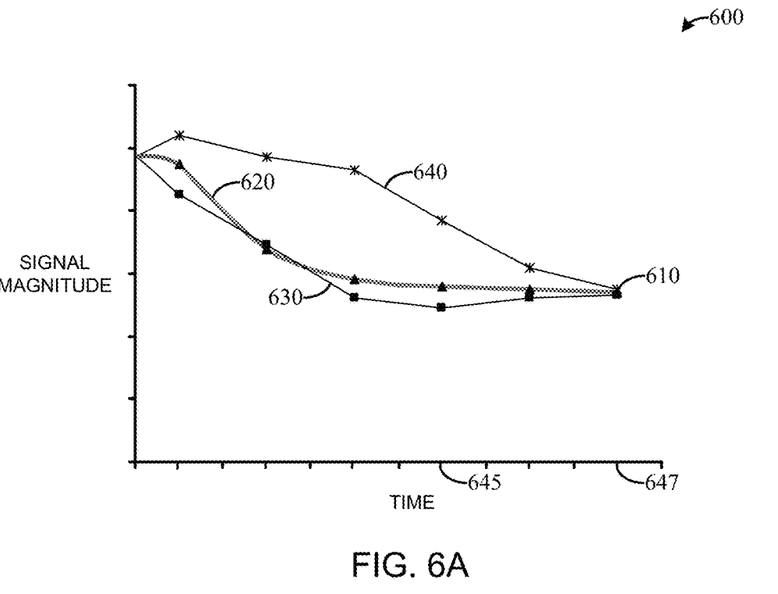
FIG. 6A shows a graph of an example of a goal improvement profile compared to an example of a subject's physiological condition.
Figure 6B:
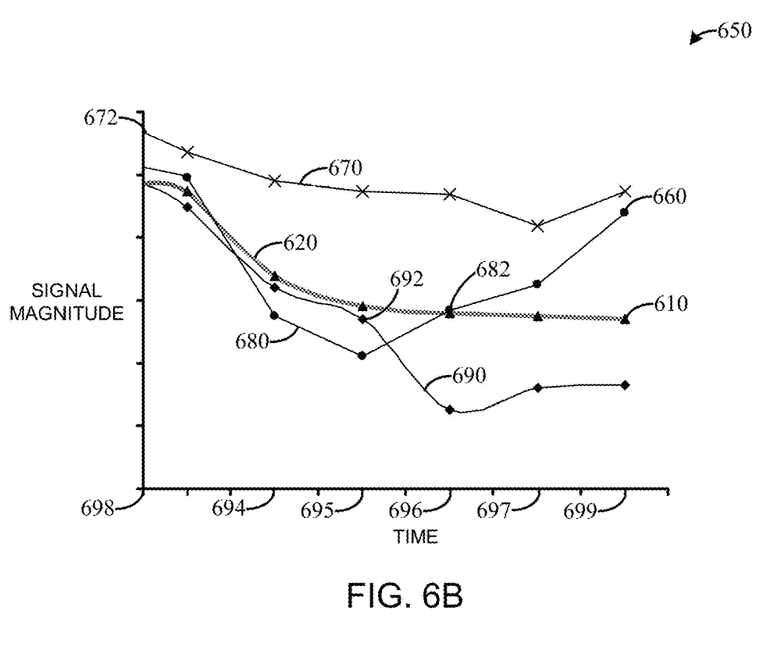
FIG. 6B shows a graph of an example of a goal improvement profile compared to an example of a subject's physiological condition.

FIGS. 6A-6B show graphs of examples that can compare a goal improvement profile to an indication of a subject's physiological condition. The graphs are shown are shown such that the x-axis represents time and the y-axis represents an indication of a measurable physiological condition of the subject 110. In FIG. 6A, a graph 600 illustrates examples of the physiological condition of the subject 630, 640 and the goal improvement profile 620, such as can be compared by a comparison circuit 145. A comparison can result in an indication of whether the subject's physiological condition has met or will meet the target condition 610 by the target time. In an example, the indication of the subject's physiological condition can be compared to a goal improvement path 620 of a goal improvement profile, such as to assess the subject's progress toward the target condition 610.

In an example, a comparison circuit 145 can compare an indication of a physiological condition of the subject 110 (e.g., path 630) to a goal improvement path 620 to determine whether the subject 110 is progressing towards the target condition 610, such as at a time 645 before the target time 647. In an example, the trajectory of the indication of the physiological condition of a subject 110 (e.g., path 640) compared to the goal improvement path 620 can indicate that the subject 110 is not adequately progressing towards the target condition 610 at one or more intermediate times before the target time. For example, the target condition can correspond to a specified weight loss within the target time period. However, a subject 110 can be unable to lose the weight due to an intervening health condition, such as a subsequent illness. However, in this example, the intervening illness can be resolved at a time 645 and the subject 110 can be shown to meet the target condition 610 by the target time.

In FIG. 6B, a graph 650 illustrates examples of the physiological condition of the subject 660, 670, 680 and the goal improvement profile 620, such as can be compared by a comparison circuit 145. The comparison can result in an indication that the physiological condition of the subject 660 did not meet the target condition 610 within the target time period. For example, the comparison of the subject's physiological condition 670 to the goal improvement profile 620 can indicate that the subject did not respond to therapy, such that the subject's physiological condition 670 remains substantially the same as the initial physiological condition 672 at a start time 698, such as at the time of a therapy or at the start of an ongoing therapy.

In an example, the comparison of the physiological condition path 680, 690 can indicate that the subject is progressing toward the target condition 610 until an intermediate time, such as the point 682, 692. In such cases, the goal improvement monitor 105 can indicate that the subject has failed to progress as expected. In an example, the goal improvement monitor 105 can be configured to determine a progress indication representative of the subject's physiological condition progressing towards meeting the target condition 610 by the target time. In an example, the progress indication can be determined by comparing the physiological condition path 680, 690 to the goal improvement profile 620 at one or more specified times or time intervals, such as at 694-697 and 699 within the target time period. For example, the comparison circuit 145 can be configured to determine a progress parameter (e.g., a Boolean value, a variable value, etc) at a specified time, such as time 694, where the value of the progress parameter is representative of the progress of the subject's physiological condition towards reaching the target condition 610 at the specified time.

In an example, the comparison circuit 145 can be configured to determine a progress parameter having a Boolean value, where a logical '1' is indicative of progress towards reaching the target condition 610, and a logical '0' is indicative of a failure to progress towards the target condition 610. In such an example, the comparison circuit 145 can compare the physiological condition path 690 to the goal improvement profile 620 at the times 694-695 and determine a progress parameter value indicative of an adequate progression (e.g., logical '1') towards reaching the target condition 610 for the times 694-695. However, when comparing the physiological condition profile 690 to the goal improvement profile 620 at time 696, the comparison circuit 145 can determine a progress parameter value having a value of logical '0' indicating that the subject's physiological condition is not adequately progressing towards the target condition 610 at the time 696.

In an example, the comparison circuit 145 can be configured to determine a progress parameter as a function (e.g. a weighting function) of one or more comparisons between the physiological condition profile 680 and the goal improvement profile 620, such as a weighting function. A weighting function can be used in situations, such as where the physiological condition profiles are noisy (e.g., the value of the physiological condition profile has high variance within a short time period), such as a weighting function configured to give greater weight to comparisons at a time closer to the target time (e.g., time 697) than a time closer to the start time (e.g., time 694). For example, the comparison circuit 145 can be configured to compute a progress parameter between the physiological condition profile 690 and the goal improvement profile 620 at the times 694-697 and 699. In an example, the progress parameter can indicate that the subject's physiological condition is adequately progressing towards the target condition 610 at times 694 and 695. At 696, the weighting function used to determine the progress parameter can still indicate that the subject is progressing towards reaching the target condition 620 although the comparison at the time 696 can indicate that the subject is not adequately progressing. The comparison at time 697 can indicate that the subject is not adequately progressing towards the target condition 620 and can be weighed into the determination of the progress parameter to indicate that the subject is no longer adequately progressing to the target condition 620.

In an example, the A/V indicator circuit 160 of a goal improvement monitor can indicate to the subject to contact a clinician for evaluation. In an example, the A/V indicator circuit 160 can provide an indication that the subject has failed to progress towards the target condition 610, such as sending a message through a communication link 330-340, where the indication can include a report detailing the physiological condition of the subject, such as containing physiological sensor data from one or more sensors associated with the subject 110.

ADDITIONAL NOTES

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc, are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, the code can be tangibly stored on one or more volatile or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment, and it is contemplated that such embodiments can be combined with each other in various combinations or permutations. The scope of the invention The claimed invention is:

1. A system for managing a chronic disease of a subject, the system comprising:
a comparison circuit, configured to determine a progress parameter using a comparison between a physiological condition of the subject detected at a specified time and a goal improvement profile at the specified time, the goal improvement profile including (1) at least one target condition indicative of an improved physiological condition detectable using a physiological sensor signal, (2) a target time when the subject is expected to reach the at least one target condition, (3) one or more predetermined intermediate target physiological conditions different than the at least one target condition and not indicating the improved physiological condition, and (4) one or more intermediate times, before the target time, when the subject is expected to reach the one or more predetermined intermediate target physiological conditions, the determined progress parameter indicating whether the physiological condition of the subject at the one or more intermediate times progresses towards reaching the target condition by the target time; and
an indication generator circuit, configured to generate an improvement indication indicating an improvement of a heart failure status based on the determined progress parameter;
wherein the comparison circuit is configured to receive the goal improvement profile prior to the indication generator circuit generating the improvement indication.

2. The system of claim 1, further comprising a goal improvement profile generator, configured to create, in the absence of the improvement indication generated by the indicator generator circuit, the goal improvement profile for the subject using at least one of a physiological data history of the subject, physiological data of a population that is comparable to the subject, or clinician input.

3. The system of claim 2, wherein the goal improvement profile generator is configured to create the goal improvement profile including an expected improvement to the physiological condition of the subject in response to a therapy provided by a caregiver.

4. The system of claim 3, wherein the goal improvement profile generator is configured to create the goal improvement profile including an improvement to the physiological condition of the subject in response to a treatment for a heart failure event.

5. The system of claim 3, wherein the goal improvement profile includes a thoracic impedance increase profile indicating an improvement of the heart failure in response to the therapy, the thoracic impedance increase profile including a target elevated thoracic impedance the subject is expected to reach at a target time elapsed after delivery of the therapy, and one or more predetermined intermediate thoracic impedance the subject is expected to reach at corresponding one or more intermediate times before the target time.

6. The system of claim 1, wherein the goal improvement profile comprises a goal improvement path over time between a start time and the target time, wherein the goal improvement path includes the at least one target condition.

7. The system of claim 1, wherein the indication generator circuit is configured to generate an indication to maintain or adjust a heart failure therapy based on the determined progress parameter.

8. The system of claim 1, wherein the determined progress parameter is determined as a weighting function of one or more comparisons between the physiological condition of the subject and the goal improvement profile at one or more of the target time or the intermediate times, and the indication generator circuit is configured to generate the improvement indication using the determined progress parameter.

9. The system of claim 1, further comprising:
an ambulatory physiological sensor, configured to determine a physiological condition of the subject using an excitation signal, the excitation signal capable of being received at one or more locations;
a communication circuit, configured to receive one or more physiological sensor signals, wherein the physiological sensor signals are representative of the physiological condition of the subject; and
a memory circuit, configured to store the goal improvement profile.

10. The system of claim 9, wherein the ambulatory physiological sensor is configured to communicate at least one of the one or more physiological sensor signals representative of the physiological condition of the subject determined from the excitation signal, wherein the physiological sensor signal is communicated using the excitation signal as a carrier.

11. An apparatus for managing a chronic disease of a subject, the apparatus comprising:
a comparison circuit, configured to determine a progress parameter using a comparison between a physiological condition of the subject detected at a specified time and a goal improvement profile at the specified time, the goal improvement profile including (1) at least one target condition indicative of an improved physiological condition detectable using a physiological sensor signal, (2) a target time when the subject is expected to reach the at least one target condition, (3) one or more predetermined intermediate target physiological conditions different than the at least one target condition and not indicating the improved physiological condition, and (4) one or more intermediate times, before the target time, when the subject is expected to reach the one or more predetermined intermediate target physiological conditions, the progress parameter indicating whether the physiological condition of the subject at the one or more intermediate times progresses towards reaching the target condition by the target time;
an indication generator circuit, configured to generate an improvement indication indicating an improvement of a heart failure status based on the determined progress parameter, and wherein the comparison circuit is configured to receive the goal improvement profile prior to the indication generator circuit generating the improvement indication;
at least two electrodes, configured to sense an impedance-indicating signal at the skin of the subject to provide the physiological sensor signal; and
an adhesive band, configured to secure the comparison circuit, the indication generator circuit, and the electrodes to the subject, such that the apparatus is configured to be capable of providing the improvement indication from an ambulatory subject and without requiring a tether to the subject.

12. The apparatus of claim 11, further comprising a communication circuit, configured to communicate the improvement indication using at least one of an audible or a visual indicator.

13. The apparatus of claim 12, wherein the communication circuit is configured to be remotely communicatively coupled, via a computer or communications network, to communicate the improvement indication.

14. The apparatus of claim 11, wherein:
the comparison circuit is configured to compare the sensed impedance-indicating signal to the goal improvement profile, the goal improvement profile including a thoracic impedance increase profile including a target elevated thoracic impedance the subject is expected to reach at a target time elapsed after delivery of a therapy, and one or more predetermined intermediate thoracic impedance the subject is expected to reach at corresponding one or more intermediate times before the target time; and
the indication generator circuit is configured to generate the improvement indication indicating an improvement of the heart failure in response to the therapy.

15. A method of using an apparatus to manage a chronic disease of a subject, the method comprising, via the apparatus:
receiving a goal improvement profile;
with a comparison circuit, automatically determining a progress parameter using a comparison between a physiological condition detected at a specified time and the goal improvement profile at the specified time, the goal improvement profile including (1) at least one target condition indicative of an improved physiological condition detectable using a physiological sensor signal, (2) a target time when the subject is expected to reach the at least one target condition, (3) one or more predetermined intermediate target physiological conditions different than the at least one target condition and not indicating the improved physiological condition, and (4) one or more intermediate times, before the target time, when the subject is expected to reach the one or more predetermined intermediate target physiological conditions, the determined progress parameter indicating whether the physiological condition of the subject at the one or more intermediate times progresses towards reaching the target condition by the target time;
with an indication generator circuit, automatically generating an improvement indication subsequent to the receiving of the goal improvement profile, the improvement indication indicating an improvement of a heart failure status based on the determined progress parameter.

16. The method of claim 15, further comprising creating, prior to automatically generating the improvement indication, the goal improvement profile for the subject using at least one of a physiological data history of the subject, physiological data of a population that is comparable to the subject, or clinician input.

17. The method of claim 16, wherein creating the goal improvement profile comprises creating a goal improvement path over time between a start time and the target time, wherein the goal improvement path includes the at least one target condition.

18. The method of claim 15, comprising automatically generating an indication to maintain or adjust a heart failure therapy based on the determined progress parameter.

19. The method of claim 15, wherein the determined progress parameter is determined as a weighting function of one or more comparisons between the physiological condition of the subject and the goal improvement profile at one or more of the target time or the intermediate times.

20. The method of claim 15, comprising determining a post-decompensation heart failure decompensation status of a subject using a physiological sensor signal.

21. The method of claim 15, comprising receiving the physiological sensor signal from a sensor configured to be associated with the subject.

22. The method of claim 21, wherein receiving the physiological sensor signal comprises extracting the physiological sensor signal from an excitation signal, the excitation signal configured to determine a characteristic associated with the physiological condition of the subject.

* * * * *